United States Patent [19]
Whitesides et al.

[11] Patent Number: 4,478,762
[45] Date of Patent: Oct. 23, 1984

[54] PROCESS FOR THE PREPARATION OF THE POTASSIUM SALT OF PHOSPHOENOLPYRUVIC ACID

[75] Inventors: George M. Whitesides, Newton; Bernard L. Hirschbein, Somerville, both of Mass.; Francois P. Mazenod, Geneva, Switzerland

[73] Assignee: Massachusetts Institute of Technology, Cambridge, Mass.

[21] Appl. No.: 416,391

[22] PCT Filed: Mar. 29, 1982

[86] PCT No.: PCT/US82/00402
§ 371 Date: Aug. 30, 1982
§ 102(e) Date: Aug. 30, 1982

[87] PCT Pub. No.: WO83/03412
PCT Pub. Date: Oct. 13, 1983

[51] Int. Cl.$^3$ ............................................. C07F 9/40
[52] U.S. Cl. ...................................... 260/983; 260/941
[58] Field of Search ................................ 260/969, 987

[56] References Cited

U.S. PATENT DOCUMENTS 2,685,552  8/1954  Stiles .................................... 260/941

FOREIGN PATENT DOCUMENTS 1151794  7/1963  Fed. Rep. of Germany ...... 260/941
3246M   4/1965  France ............................... 260/941
56-87589 7/1981  Japan .................................. 260/987

OTHER PUBLICATIONS

Webster et al., "Biochem. J.", (1976), 155, pp. 433–441.
Kosolapoff et al., "Organic Phosphorus Compounds", vol. 6, (1974), pp. 260–261.

Primary Examiner—Anton H. Sutto
Attorney, Agent, or Firm—Arthur A. Smith, Jr.; Thomas J. Engellenner

[57] ABSTRACT

The potassium salt of phosphoenolpyruvic acid (PEP-K), used as a phosphorylation agent particularly in enzymatic reactions, is prepared by a process which consists of two steps, namely the treatment of a halopyruvic acid with a trialkyl phosphite and the hydrolysis of the dialkyl phosphate of enolpyruvic acid thus formed in an aqueous medium and in the presence of potassium hydroxide.

4 Claims, No Drawings

PROCESS FOR THE PREPARATION OF THE POTASSIUM SALT OF PHOSPHOENOLPYRUVIC ACID

This application is based upon, and claims the priority of, International Application No. PCT/US82/00402 which was filed Mar. 29, 1982.

TECHNICAL FIELD

This invention relates to organic chemical synthesis and, in particular, synthesis of phosphorlyating agents.

BACKGROUND ART

Phosphoenolpyruvic acid (PEP) represents a particularly efficient phosphorylation agent, especially for organic syntheses promoted by enzymatic catalysis in which it is desired to regenerate the ATP or adenosine triphosphate. It thus constitutes a useful alternative to acetyl phosphate (AcP), over which it has a number of advantages. In fact, PEP is recognized as a more powerful phosphorylation agent than AcP, it is more stable in solution, and it, therefore, is used more easily, particularly in semi-industrial applications.

This invention concerns a process of the preparation of phosphoenolpyruvic acid in the form of its potassium salt, or PEP-K. Since the potassium is inert towards most enzymatic systems, and its presence is even necessary, for example, to release the activity of pyruvic kinase, the salt thus obtained can be used directly in phosphorylation processes.

SUMMARY OF THE INVENTION

The process of the invention consists of two steps carried out consecutively, as follows:
 a. The treatment of a halopyruvic acid with a trialkyl phosphite to provide a dialkyl phosphate of enolpyruvic acid of the formula

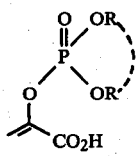

in which the symbols R, taken separately, represent a lower alkyl radical, or taken together, represent a lower alkylenyl radical, and
 b. Hydrolysis of the compound thus obtained in an aqueous medium in the presence of potassium hydroxide.

The process of the invention can be illustrated with the use of the following scheme:

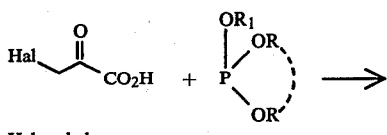

Hal = halogen
R₁ = lower alkyl

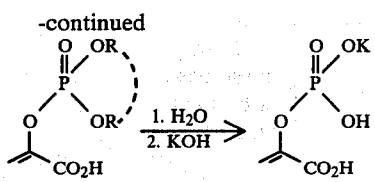

(PEP-K)

The potassium salt thus obtained, insoluble in the reaction medium, can easily be separated from the reaction mixture by simple filtration and can thus be used directly as a phosphorylation reagent.

In this regard, in order to establish its activity, a sample of the product prepared by the process of the invention was used to synthesize glucose-6-phosphate. The method followed is specified in detail below.

A solution of 0.800 mole of glucose, 0.800 mole of PEP-K 35 mmoles of magnesium chloride, and 10 mmoles of 2-mercaptoethanol in 800 ml of distilled water was brought to pH 7.6 with solid KOH, and was then transferred into a 2-liter 3-necked flask equipped with a pH-measuring electrode and a magnetic stirrer. The solution was degassed by a stream of argon, and 1.20 mmoles of ATP and an aqueous suspension (0.78 liter) of pyruvic kinase (1260 U) and of hexokinase (863 U) (each enzyme being previously immobilized in a polyacrylamide gel—see J. Am. Chem. Soc. 102, 6324, [1980] —) were then added to it under an argon atmosphere. The reaction mixture, held at 20° C. and at pH 7.5–7.6 by the occasional addition of several drops of 12 M HCl, was stirred for 8.5 days. The biochemical tests carried in accordance with the methods described by H. V. Bergmeyer in "Methods of Enzymatic Analysis", Verlag Chemie Weinheim, Academic Press, N.Y. (1974), showed the presence of 0.77 mole of glucose-6-phosphate G-6-P (yeild 96%).

As indicated above, the substituents R can represent either a lower alkyl radical, preferably methyl or ethyl, or a bivalent alkylenyl radical, such as —CH₂—CH₂—, for example. Thus, for example, trimethyl phosphite, triethyl phosphite, or methyl ethylene phosphite can be used as the trialkyl phosphite, with trimethyl phosphite being preferred.

As the halopyruvic acid, chloropyruvic or bromopyruvic acid can be used. These compounds can be obtained by known procedures.

The first step of the process of the invention is carried out in an organic medium, in the presence of a solvent such as an ether, diethyl ether, for example, an ester such as ethyl acetate, or an aromatic hydrocarbon, for example, toluene or benzene. The best yields have been observed when using diethyl ether.

The yields of the following step, which consists of the hydrolysis of the phosphate obtained, depend to a great extent on the quantity of potassium hydroxide used. Thus, the optimal value of the pH is approximately 1.7–2.8, which corresponds to a quantity of potassium hydroxide equal to approximately 0.70–0.90 equivalents based on the initial quantity of halolpyruvic acid used.

The potassium phosphoenolpyruvate obtained by the process of the invention is present in the form of a non-hygroscopic crystalline product. It is stable and of high purity, and it can be used directly in enzymatic syntheses without prior purification. The process of the invention accordingly offers definite advantages over the known methods of preparation of PEP.

Among these advantages, it is appropriate to stress the fact that by the process of the invention, the direct precipitation of the potassium salt formed is obtained in the hydrolysis mixture itself. The uneconomical evaporation of large volumes of water is thus avoided, as well as the precipitation of the monocyclohexylammonium salt and the ion exchange resin treatment such as that described by Clark and Kirby— see the scheme below.

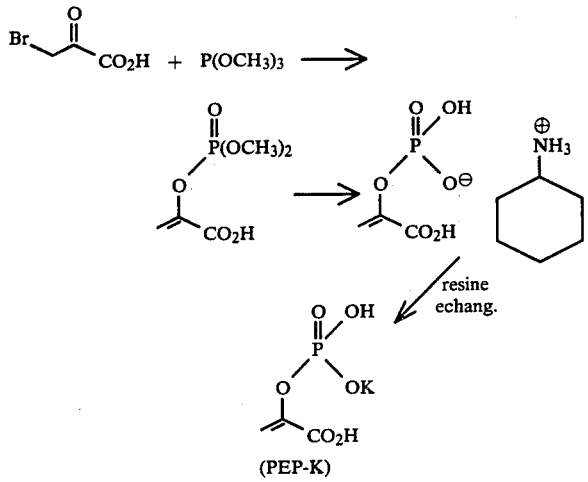

(PEP-K)

DESCRIPTION OF THE PREFEREED EMBODIMENT

The invention is illustrated in further detail by the following example, in which the temperatures are indicated in degrees Centigrade.

EXAMPLE a. Dimethyl Phosphate of 2-hydroxyacrylic Acid. A solution of 752 g (4.37 moles) of bromopyruvic acid (purity 97%) obtained by the method described in Biochem. Prep. 11, 101-104 (1966)] in 1.25 liters of anhydrous ether was added dropwise over a period of 3.5 h and with stirring to a solution of 557 ml (4.72 moles) of trimethyl phosphite in 3.85 liters of anhydrous ether. The rate of addition was adjusted so as to keep the ether under constant reflux. After having continued the stirring at room temperature for 1 hour, the mixture was concentrated under reduced pressure to obtain 1002 g of a brown viscous oil composed of the desired product.

b. PEP-K. The oil obtained by the method described under a. above, was dissolved in 1.67 liters of distilled water and kept at 20° with stirring for 15 h. The spontaneous hydrolysis observed during this period produces 2.64 moles of PEP (yield 60%). The solution was cooled in an ice bath, and 267 g of solid KOH (purity 80%; 4.0 moles) was then added, followed by 2.7 liters of anhydrous ethanol. The white precipitate thus formed was collected by filtration, washed with 800 ml of cold anhydrous ethanol, and dried at 13.3 Pa to obtain 531 g of PEP-K (purity 95%; 2.45 moles, yield 50% based on the weight of pyruvic acid used as the starting material).

Optimization tests were made by carrying out the reaction with various quantities of KOH. The following table the summarizes the results obtained.

| Equivalents of KOH (*) | pH | Yields of PEP-K (%) |
|---|---|---|
| Starting with bromopyruvic acid | | |
| 0.73 | 1.7 | 61 |
| 0.93 | 2.8 | 62 |
| 1.0 | 3.2 | 56 |
| 1.1 | 3.4 | 58 |
| 1.5 | 4.4 | 20 |
| Starting with chloropyruvic acid | | |
| 1.0 | 2.8 | 41 |
| 1.2 | 3.4 | 30 |
| 1.4 | 3.8 | 26 |
| 1.5 | 4.1 | 16 |
| 2.0 | 5.5 | (**) |

(*) Based on initial quantity of halopyruvic acid
(**) The PEP-K does not precipitate, but separates in the form of an oil instead

We claim:
1. Process for the preparation of the potassium salt of phosphoenolpyruvic acid (PEP-K) of the formula

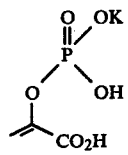

characterized by the fact that the two following reaction steps are carried out consecutively:
a. The treatment of a halopyruvic acid with a trialkyl phosphite to obtain a dialkyl phosphate of enolpyruvic acid of the formula

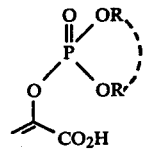

wherein the symbols R, taken separately, represent a lower alkyl radical, or taken together, represent a lower alkylenyl radical, and
b. Hydrolysis of the compound thus obtained in an aqueous medium and in the presence of potassium hydroxide.

2. Process pursuant to claim 1, characterized by the fact that trimethyl phosphite or methyl ethylene phosphite is used as the trialkyl phosphite.

3. Process pursuant to claim 1, characterized by the fact that the reaction which defines Step a. of the process is carried out in diethyl ether.

4. Process pursuant to claim 1, characterized by the fact that the potassium hydroxide is used in the amount of 0.70 to 0.95 equivalents based on the initial halopyruvic acid.

* * * * *